(12) United States Patent
Weissman et al.

(10) Patent No.: US 7,641,897 B2
(45) Date of Patent: Jan. 5, 2010

(54) FEEDER LAYER AND SERUM INDEPENDENT EMBRYONIC STEM CELLS

(75) Inventors: Irving L. Weissman, Redwood City, CA (US); Toshiyuki Yamane, Menlo Park, CA (US); Scott Dylla, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 247 days.

(21) Appl. No.: 11/286,088

(22) Filed: Nov. 23, 2005

(65) Prior Publication Data

US 2006/0172414 A1 Aug. 3, 2006

Related U.S. Application Data

(60) Provisional application No. 60/630,850, filed on Nov. 23, 2004.

(51) Int. Cl.
*A61K 48/00* (2006.01)
*C12N 5/16* (2006.01)
*C12N 15/00* (2006.01)

(52) U.S. Cl. ............... 424/93.21; 435/455; 435/377
(58) Field of Classification Search .............. None
See application file for complete search history.

(56) References Cited

U.S. PATENT DOCUMENTS 5,942,435 A * 8/1999 Wheeler ............ 435/325

OTHER PUBLICATIONS

Sato et al. (2004) Nat. Med. 10:55-63.*
Humphrey et al. (2004) Stem Cells 22: 522-530.*
Shim et al. (2004) J. Neurosci 24:843-852.*
Sun et al. (1999) Proc. Natl. Acad. Sci. 96:6199-6204.*
Haraguchi et al. (2000) J. Exp. Med. 191:1709-1720.*
Akashi, K. et al., Bcl-2 Rescues T Lymphopoiesis in Interleukin-7 Receptor-Deficient Mice, (1997) Cell 89, 1033-1041.
Domen, J. et al., Hematopoietic Stem Cells Need Two Signals to Prevent apoptosis; BCL-2 Can Provide One of These, Kitl/c-Kit Signaling the Other, (2000) J. Exp. Med. 192, 1707-1718.
Fairbairn, L. J. et al., Suppression of Apoptosis Allows Differentiation and Development of a Multipotent Hemopoietic Cell Line in the Absence of Added Growth Factors, (1993) Cell 74, 823-832.
Finley, M. F. et al., BMP-4 Inhibits Neural Differentiation of Murine Embryonic Stem Cells, (1999) Neurobiology 40, 271-287.
Johansson, B. M. et al., Evidence for Involvement of Activin A and Bone Morphogenetic Protein 4 in Mammalian Mesoderm and Hematopoietic Development, (1995) Mol. Cell. Biol. 15, 141-151.
Kondo, M. et al., Bcl-2 Rescues T Lymphopoiesis, but Not B or NK Cell Development, in Common γ Chain-Deficient Mice, (1997) Immunity 7, 155-162.
Lagasse, E. et al., Enforced Expression of Bcl-2 in Monocytes Rescues Macrophages and Partially Reverses Osteopetrosis in op/op Mice, (1997) Cell 89, 1021-1031.
Miyazawa, K. et al., Two major Smad pathways in Tcf-β superfamily signaling, (2002) Genes Cells 7, 1191-1204.
Opferman, J. T. et al., Apoptosis in the development and maintenance of the immune system, (2003) Nat. Immunol. 4, 410-415.
Qi, X. et al., BMP4 supports self-renewal of embryonic stem cells by inhibiting mitogen-activated protein kinase pathways, (2004) Proc. Natl. Acad. Sci. USA 101, 6027-6032.
Reya, T. et al., A role for Wnt signaling in self-renewal of haematopoietic stem cells, (2003) Nature 423, 409-414.
Yamane et al., Development of Osteoclasts From Embryonic Stem Cells Through a Pathway That Is c-*fms* but not c-*kit* Dependent, (1997) Blood 90:3516-3523.
Yamane, T. et al., Derivation of Melanocytes From Embryonic Stem Cells in Culture, (1999) Dev. Dyn. 216, 450-458.
Ying et al., BMP Induction of Id Proteins Suppresses Differentiation and Sustains Embryonic Stem Cell Self-Renewal in Collaboration with STAT3, (2003) Cell 115, 281-292.

* cited by examiner

*Primary Examiner*—Joanne Hama
(74) *Attorney, Agent, or Firm*—Bozicevic, Field & Francis LLP; Pamela J. Sherwood

(57) ABSTRACT

Undifferentiated primordial stem cells are manipulated to permit their long term growth in defined media lacking serum and feeder layer cells by shifting the apoptotic balance of the cells, through increasing the activity of Bcl-2 family anti-apoptotic proteins or decreasing the activity of Bcl-2 family pro-apoptotic proteins. In some embodiments of the invention, the Bcl family protein is Bcl-2. The ES cells sustain the characteristics of undifferentiated, pluripotent stem cells during long-term serum- and feeder layer cell-free conditions, including the ability to be expanded in vitro, but maintain their potential to differentiate into mature cell types.

3 Claims, 5 Drawing Sheets

SEQUENCE LISTING

<160> NUMBER OF SEQ ID NOS: 10

<210> SEQ ID NO 1
<211> LENGTH: 20
<212> TYPE: DNA
<213> ORGANISM: mouse

-continued

```
<400> SEQUENCE: 1
tctgggaacg cctcatcaat                                               20

<210> SEQ ID NO 2
<211> LENGTH: 19
<212> TYPE: DNA
<213> ORGANISM: mouse

<400> SEQUENCE: 2
ggagaggcag cctctgtgc                                                19

<210> SEQ ID NO 3
<211> LENGTH: 20
<212> TYPE: DNA
<213> ORGANISM: mouse

<400> SEQUENCE: 3
gcgacatttt ctggtgcaca                                               20

<210> SEQ ID NO 4
<211> LENGTH: 20
<212> TYPE: DNA
<213> ORGANISM: mouse

<400> SEQUENCE: 4
tcgaacgtgc actgatacgg                                               20

<210> SEQ ID NO 5
<211> LENGTH: 20
<212> TYPE: DNA
<213> ORGANISM: mouse

<400> SEQUENCE: 5
ggcaaattca acggcacagt                                               20

<210> SEQ ID NO 6
<211> LENGTH: 21
<212> TYPE: DNA
<213> ORGANISM: mouse

<400> SEQUENCE: 6
tcgctcctgg aagatggtga t                                             21

<210> SEQ ID NO 7
<211> LENGTH: 20
<212> TYPE: DNA
<213> ORGANISM: mouse

<400> SEQUENCE: 7
cagccctaca gccacatgat                                               20

<210> SEQ ID NO 8
<211> LENGTH: 19
<212> TYPE: DNA
<213> ORGANISM: mouse

<400> SEQUENCE: 8
tttagccctc cgatgaggc                                                19

<210> SEQ ID NO 9
<211> LENGTH: 20
<212> TYPE: DNA
```

```
<213> ORGANISM: mouse

<400> SEQUENCE: 9
gtaccacagg cattgtgatg                                               20

<210> SEQ ID NO 10
<211> LENGTH: 20
<212> TYPE: DNA
<213> ORGANISM: mouse

<400> SEQUENCE: 10
tagtgatgac ctggccgtca                                               20
```

FEEDER LAYER AND SERUM INDEPENDENT EMBRYONIC STEM CELLS

This invention was made with Government support under contract CA86065 awarded by the National Institutes of Health. The Government has certain rights in this invention.

BACKGROUND OF THE INVENTION

Stem cells are defined as cells that, at the single cell level, are capable of both self-renewal and differentiation to specialized cell types. The growth potential of mammalian embryonic stage cells have been known for many years, although the ability to culture such pluripotent and totipotent stem cells, particularly human stem cells, has only been recently developed. Embryonic stem (ES) cells are derived from cultures of inner cell mass (ICM) cells, and have the property of participating as totipotent cells when placed into host blastocysts. The developmental pathways that endogenous ICM cells or transferred ES cells take to tissue formation and organogenesis may be controlled for the development of tissue and organ specific stem cells. The ability of ES cells to grow specialized cells and tissues could provide an unprecedented tool in the clinic, by providing a means for transplantation and repair of damaged muscles, nerves, organs, bones and other tissues. ES cell lines also have a potent ability to replicate in culture, unlike many of the somatic stem cells, which may also be limited to differentiation within specific lineages.

When cultured in vitro, ES cells can self-renew indefinitely in the presence of LIF and fetal bovine serum or mouse feeder layer cells, resulting in daughter cells that maintain their potential for multilineage differentiation. In general, when ES cells are maintained in serum- and feeder-free conditions, the number of undifferentiated cells quickly reaches a plateau and begins to decline after only a couple of passages, and a population of cells with a non-ES cell morphology arises in culture despite the presence of LIF. Thus, additional signals from serum or feeders appear to be required to fully support the self-renewal of ES cells.

Serum and feeder cells may act to provide the survival signals manifest in growth factors and cytokines, and such extrinsic survival signals can be especially critical in low cell density conditions. Where such stimulation through auto- and paracrine factors is inadequate, ES cells may become apoptotic.

It has been suggested that the use of N2 and B27 supplemented media to expand ES cells in serum- and feeder-free conditions improves viability. However, these supplements alone cannot support the self-renewal of ES cells. Further, as N2 and B27 supplements contain hormones (corticosterone, progesterone, and T3) and retinyl acetate, a precursor of retinoic acid, (which components may induce differentiation of ES cells), the presence of these components complicates the analysis of cytokines, growth factors, and chemicals on self-renewal and differentiation of ES cells. To analyze the effect of single cytokines, growth factors, and other molecules on self-renewal and differentiation of ES cells, it would optimal if cells could be protected from apoptotic cell death in serum- and feeder-free conditions.

The therapeutic use of stem cells will benefit from the ability to culture the cells in defined media. Such media may have the advantage of being free from feeder layer cells, which have a potential for virus contamination. Such media may also be free of serum, which adds cost, complexity, and a potential for prion contamination. The present invention addresses this problem.

SUMMARY OF THE INVENTION

Compositions and methods are provided for the culture of embryonic stem cells in serum- and feeder layer cell-free conditions. The ES cells sustain the characteristics of undifferentiated, pluripotent stem cells during long-term culture, including the ability to be expanded in vitro, but maintain their potential to differentiate into mature cell types. The cells are manipulated to permit their long term growth in such defined media by shifting the apoptotic balance of the cells, through increasing the activity of anti-apoptotic proteins, e.g. Bcl-2; Mcl-1; etc.; or decreasing the activity of pro-apoptotic proteins, e.g., Bad, Bax, etc. Such manipulation may be achieved through transient changes, e.g. providing exogenous anti-apoptotic proteins to the cells; administration of small molecule modulators; providing RNAi or anti-sense sequences specific for pro-apoptotic proteins; and the like. Alternatively, the changes may be permanent, e.g. integration of a genetic construct encoding a polypeptide providing Bcl-2 activity into the genome of the cell.

The expanded cell populations are useful as a source of stem cells, e.g. to reconstitute function in a host that is deficient in a particular cell lineage or lineages; for experimental and screening purposes; and the like.

DETAILED DESCRIPTION OF THE EMBODIMENTS

Figure 1:
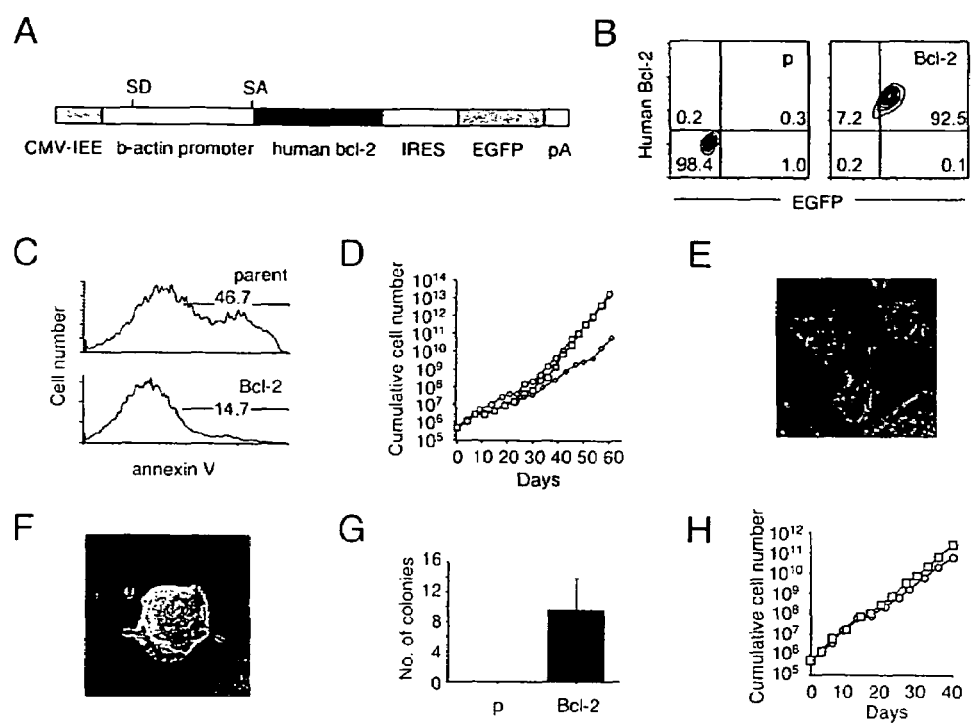
FIG. 1A-1H. Serum and feeder layer-independent growth of ES cell clones overexpressing Bcl-2. (A) Construction of Cag-human Bcl-2-IRES-EGFP plasmid. (B) Expression of human Bcl-2 (Y-axis) and EGFP (X-axis) in a representative Bcl-2 clone (right panel). The parental clone (left panel) is shown as a control. (C) Annexin V staining. Parental (Upper panel) or Bcl-2 (lower panel) ES cells were cultured in serum and feeder-free conditions for 3 days and the percentage of annexin-V+ cells as visualized by flow cytometry is denoted. (D) Growth curve of three independent Bcl-2 ES cell clones in serum and feeder-free conditions in X-Vivo media. (E) Colonies of a Bcl-2 clone growing independent of serum and feeders. (F) A representative colony formed under low cell density conditions. (G) Colony formation activity of parental (p) and Bcl-2 ES cells plated at a density of 200 cells per well (12 well-plate). Colonies were counted 7 days later and values are expressed as the mean±s.d. (H) Growth curve of two independent Bcl-2 clones in IMDM/F12-based media.

ES cells sustain the characteristics of undifferentiated, pluripotent stem cells during long-term serum- and feeder layer cell-free conditions, including the ability to be expanded in vitro, but maintain their potential to differentiate into mature cell types. Defined media for the culture of the ES cells may include insulin, transferrin, and albumin as basic supplements for serum-free cultures, but preferably no other proteins or hormones. The cells can expand in such media in the presence of LIF, and do not require the presence of bone morphogenic proteins (BMPs), growth and differentiation factors (GDFs), or an extracellular protein matrix derived from feeder layer cells.

The ES cells are manipulated to permit their long term growth in such defined media by shifting the apoptotic balance of the cells, through increasing the activity of anti-apoptotic proteins, e.g. Bcl-2; Bcl-X, Mcl-1, etc.; or decreasing the activity of pro-apoptotic proteins, e.g., Bax, Bad, etc. The activity levels of such Bcl-2 family members may be manipulated by providing exogenous protein to the cell, by introduction into the cell of a genetic construct encoding the protein of interest, or by introduction of small molecules that potentiates or inhibits activity of a Bcl-2 family member (see O'Neill and Hockenbery (2003) Current Medicinal Chemistry 10:1553-1562, "Bcl-2-Related Proteins as Drug Targets", herein incorporated by reference). In some embodiments of the invention, the Bcl-2 family protein is at least a portion of Bcl-2, where the portion provides all or part of native Bcl-2 activity.

Cultures that provide ES cell activity can be maintained for at least three weeks, frequently six weeks and can be eight weeks or more. The culture media that are employed are conventional media for the growth of mammalian cells, preferably in the absence of serum, using only defined protein factors. In the absence of the modulation of apoptotic protein activity, the medium is inefficient at maintaining growth and expansion of the ES cells.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

Apoptotic Balance; and Bcl Family Proteins. The Bcl-2 family of proteins provides an intracellular checkpoint of apoptosis. The founding member of this family is the apoptosis-inhibiting protein encoded by the Bcl-2 protooncogene. Bcl-2 protein is a 25 kD, integral membrane protein localized to intracellular membranes including mitochondria. This factor extends survival in many different cell types by inhibiting apoptosis elicited by a variety of death-inducing stimuli. The genetic sequence of human Bcl-2 is available at Genbank, accession number M14745.

The family of Bcl-2-related proteins is comprised of both anti-apoptotic and pro-apoptotic members that function in a distal apoptotic pathway common to all multi-cellular organisms. The ratio of anti-apoptotic (Bcl-2, Bcl-xL, Mcl-1 and A1) to pro-apoptotic (Bax, Bak, Bcl-xS, Bad, Bik and Bid) molecules are involved in determining whether a cell will respond to a proximal apoptotic stimulus; which ratio may be referred to herein as the apoptotic balance. Because members of this family can form both homodimers and heterodimers, the latter often between anti- and pro-apoptotic polypeptides, the balance of these homodimers and heterodimers play a role in regulating apoptosis.

Members of the Bcl-2 family have been defined by sequence homology that is largely based upon conserved motifs termed Bcl-Homology domains. Bcl-Homology domains 1 and 2 (BH1 and BH2) domains have been shown to be important in dimerization and in modulating apoptosis. A third homology region, BH3, has been found in some family members and shown to be important in dimerization as well as promoting apoptosis. BH4, the most recently identified homology domain, is present near the amino terminal end of some pro-apoptotic family members.

All known members of the Bcl-2 family other than Bad and Bid have a C-terminal membrane-anchoring tail (TM). Bcl-2 family members with a TM are intracellular integral membrane proteins localized to mitochondria, the endoplasmic reticulum and the nuclear membrane. The intracellular membrane localization of BCL-2 family members together with the identification of structural similarity between the Bcl-xL monomer and the ion-pore forming toxins of colicin and diphtheria toxin B fragment has prompted electrophysiological studies by several groups on the ability of Bcl-2 family members to form ion channels in artificial lipid membranes.

Genetic sequences of the Bcl-2 family of proteins are known in the art. For example, the sequence of human Bcl-2-related ovarian killer protein (BOK) is available at Genbank, accession number AF174487. Human Bax alpha sequence is available at Genbank, accession number L22473. Human Bax beta sequence is available at Genbank, accession number L22474. Human Bax gamma sequence is available at Genbank, accession number L22475. Human BAX delta sequence is available at Genbank, accession number U19599. Human Bcl-xL sequence is available at Genbank, accession number Z23115. Human Bcl-xS sequence is available at Genbank, accession number Z23116. Human bcl-xL/bcl-2 associated death promoter (BAD) sequence is available at Genbank, accession number AF031523. The human myeloid cell differentiation protein (MCL1) is available at Genbank, accession number L08246.

The sequence of the Bcl-2 family member polypeptide may be altered in various ways known in the art to generate targeted changes in sequence. The polypeptide may be substantially similar to the native sequences, i.e. will differ by at least one amino acid, and may differ by at least two but not more than about ten amino acids. Deletions may further include larger changes, such as deletions of a domain or exon, providing for active peptide fragments of the protein. Other modifications of interest include tagging, e.g. with the FLAG system, HA, green fluorescent protein, etc. Such alterations may be used to alter properties of the protein, by affecting the stability, specificity, etc. The protein may be joined to a wide variety of other oligopeptides or proteins for a variety of purposes, particular for facilitating transport across membranes.

The ability of a domain or fragment of a polypeptide to provide feeder layer independence to an ES cell can be determined by empirical methods, e.g. by introducing a candidate construct into an ES cell and culturing the cell in the absence of said feeder layer cells. In some embodiments of the invention, the heterologous sequence may be used, e.g. mouse bcl-2 to regulate human ES cells; human Bcl-2 to regulate mouse ES cells; etc. Alternatively, a truncated or otherwise altered form of the protein that lacks the full activity of the endogenous protein may be used.

Techniques for in vitro mutagenesis of cloned genes are known. Examples of protocols for scanning mutations may be found in Gustin et al., Biotechniques 14:22 (1993); Barany, Gene 37:111-23 (1985); Colicelli et al., Mol Gen Genet 199: 537-9 (1985); and Prentki et al., Gene 29:303-13 (1984). Methods for site specific mutagenesis can be found in Sambrook et al., Molecular Cloning: A Laboratory Manual, CSH Press 1989, pp. 15.3-15.108; Weiner et al., Gene 126:35-41 (1993); Sayers et al., Biotechniques 13:592-6 (1992); Jones and Winistorfer, Biotechniques 12:528-30 (1992); Barton et al., Nucleic Acids Res 18:7349-55 (1990); Marotti and Tomich, Gene Anal Tech 6:67-70 (1989); and Zhu Anal Biochem 177:120-4 (1989).

Expression construct: In one embodiment of the invention, the apoptotic balance is altered by delivering to the targeted ES cells an exogenous nucleic acid expression vector. The vector may encode all or part of an anti-apoptotic Bcl-2 family protein; or may encode anti-sense or RNAi specific for a pro-apoptotic Bcl-2 family member. Many vectors useful for transferring exogenous genes into target mammalian cells are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc.

Retrovirus based vectors may be used. For example, see Baum et al. (1996) J Hematother 5(4):323-9; Schwarzenberger et al. (1996) Blood 87:472478; Nolta et al. (1996) P.N.A.S. 93:2414-2419; and Maze et al. (1996) P.N.A.S. 93:206-210. Lentivirus vectors have also been described for use with stem cells, for example see Mochizuki et al. (1998) J Virol 72(11):8873-83. The use of adenovirus based vectors with stem cells has also been published, see Ogniben and Haas (1998) *Recent Results Cancer Res* 144:86-92.

Various techniques known in the art may be used to transfect the target cells, e.g. electroporation, calcium precipitated DNA, fusion, transfection, lipofection and the like. The particular manner in which the DNA is introduced is not critical to the practice of the invention. Such methods may utilize carrier molecules, including calcium-phosphate, DEAE dextran and cationic lipids. Nucleic acids can be adsorbed to unilamellar liposome vesicles comprising cationic lipids mixed with neutral lipids, which vesicles may be modified by the inclusion of various commercially available components, e.g. FuGENE 6; X-tremeGENE Q2; etc. (Roche Applied Science). Cationic polymers, including dendrimeric polyamines or homopolymers of positively charged amino acids such as poly-L-lysines, poly-D-lysines and poly-L-ornithines, HIV tat, *Pseudomonas* exotoxin, *Drosophila* Antennapedia and HSV-1 VP22 protein may also be used as carriers. Agents that enhance uptake may be covalently conjugated to the probes. Examples include cationic peptides, cholesterol, arginine-rich peptides, etc.

Combinations of retroviruses and an appropriate packaging line may be used, where the capsid proteins will be functional for infecting the target cells. Usually, the cells and virus will be incubated for at least about 24 hours in the culture medium. Commonly used retroviral vectors are "defective", i.e. unable to produce viral proteins required for productive infection. Replication of the vector requires growth in the packaging cell line.

The host cell specificity of the retrovirus is determined by the envelope protein, env (p120). The envelope protein is provided by the packaging cell line. Envelope proteins are of at least three types, ecotropic, amphotropic and xenotropic. Retroviruses packaged with ecotropic envelope protein, e.g. MMLV, are capable of infecting most murine and rat cell types. Ecotropic packaging cell lines include BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse. Amphotropic packaging cell lines include PA12 (Miller et al. (1985) Mol. Cell. Biol. 5:431-437); PA317 (Miller et al. (1986) Mol. Cell. Biol. 6:2895-2902) GRIP (Danos et al. (1988) PNAS 85:6460-6464). Retroviruses packaged with xenotropic envelope protein, e.g. AKR env, are capable of infecting most mammalian cell types, except murine cells.

The sequences at the 5' and 3' termini of the retrovirus are long terminal repeats (LTR). A number of LTR sequences are known in the art and may be used, including the MMLV-LTR; HIV-LTR; AKR-LTR; FIV-LTR; ALV-LTR; etc. Specific sequences may be accessed through public databases. Various modifications of the native LTR sequences are also known. The 5' LTR acts as a strong promoter, driving transcription of a gene after integration into a target cell genome. For some uses, however, it is desirable to have a regulatable promoter driving expression. Where such a promoter is included, the promoter function of the LTR will be inactivated. This is accomplished by a deletion of the U3 region in the 3' LTR, including the enhancer repeats and promoter, which is sufficient to inactivate the promoter function. After integration into a target cell genome, there is a rearrangement of the 5' and 3' LTR, resulting in a transcriptionally defective provirus, termed a "self-inactivating vector".

Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold. Various promoters are known that are expressed in ES cells, e.g. Oct-4, SSEA promoters, etc.

In some embodiments of the invention, the genetic constructs are those that can be removed from the target cells after expansion. This can be accomplished by the use of a transient vector system, or by including a heterologous recombination site that flanks the coding sequence. In this manner, after expansion the construct can be removed prior to use of the expanded cell population. Preferably a detectable marker, e.g. green fluorescent protein, luciferase, cell surface proteins suitable for antibody selection methods, etc. is included in the expression vector, such that after deletion of the construct the cells can be readily isolated that lack the exogenous sequence.

The term "heterologous recombination site" is meant to encompass any introduced genetic sequence that facilitates site-specific recombination. In general, such sites facilitate recombination by interaction of a specific enzyme with two such sites. Exemplary heterologous recombination sites include, but are not necessarily limited to, lox sequences with recombination mediated by Cre enzyme; frt sequences (Golic et al. (1989) *Cell* 59:499-509; O'Gorman et al. (1991) *Science* 251:1351-5; recombination mediated by the FLP recombinase), the recognition sequences for the pSR1 recombinase of *Zygosaccharomyces rouxii* (Matsuzaki et al. (1990) *J. Bacteriol.* 172:610-8), and the like.

Sequences encoding lox sites are of particular interest for use in the present invention. A lox site is a nucleotide sequence at which the gene product of the cre gene, referred to herein as "Cre," catalyzes site-specific recombination. A particularly preferred lox site is a loxP site. The sequence of loxP, which is 34 bp in length, is known and can be produced synthetically or can be isolated from bacteriophage P1 by methods known in the art (see, e.g. Hoess et al. (1982) *Proc. Natl. Acad. Sci. USA* 79:3398). The loxP site is composed of two 13 bp inverted repeats separated by an 8 bp spacer region. Other suitable lox sites include loxB, loxL, and loxR, which can be isolated from *E. coli* (Hoess et al. (1982) Proc. Natl. Acad. Sci. USA 22:3398).

In an alternative method, expression vectors that provide for the transient expression in mammalian cells may be used. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient short term expansion of cells, but do not affect the long term genotype of the cell.

Exogenous polypeptides: In some cases it is desirable to provide exogenous protein, rather than transducing the cells with an expression construct. Preferably the protein, e.g. Bcl-2 protein, is modified so as to increase its transport into the cells, or is encapsulated to enhance transport into the cell, for example in a lipid vesicle.

In one embodiment of the invention, tat protein is used for delivery. The preferred transport polypeptides are characterized by the presence of the tat basic region amino acid sequence (amino acids 49-57 of naturally-occurring tat protein); the absence of the tat cysteine-rich region amino acid sequence (amino acids 22-36 of naturally-occurring tat protein) and the absence of the tat exon 2-encoded carboxy-terminal domain (amino acids 73-86 of naturally-occurring tat protein). Transport polypeptides are attached to protein by chemical cross-linking or by genetic fusion. A unique terminal cysteine residue is a preferred means of chemical cross-linking. Alternatively, cationic polymers, including dendrimeric polyamines or homopolymers of positively charged amino acids such as poly-L-lysines, poly-D-lysines and poly-L-ornithines, *Pseudomonas* exotoxin, *Drosophila* Antennapedia and HSV-1 VP22 protein may be used as carriers.

Alternatively, liposomes of various compositions may be exploited as delivery vehicle for the proteins (see Witschi et al. (1999) Pharm. Res., 16: 382-390; Yeh et al. (1996) Pharm. Res., 13: 1693-1698). The interaction of the protein with liposomes usually relies on hydrophobic interactions or charge attraction. The latter is in particular the case when using cationic lipid delivery systems. For example, a cationic lipid can effectively deliver a variety of proteins by caveolar-mediated entry. Of particular interest are mitochondrial targeted drug delivery systems, e.g. see Weissig (2003) Crit Rev Ther Drug Carrier Syst. 20(1):1-62, herein incorporated by reference.

Stem cells. Pluripotent stem cells are cells derived from any kind of tissue (usually embryonic tissue such as fetal or pre-fetal tissue), which stem cells have the characteristic of being capable under appropriate conditions of producing progeny of different cell types that are derivatives of all of the 3 germinal layers (endoderm, mesoderm, and ectoderm). These cell types may be provided in the form of an established cell line, or they may be obtained directly from primary embryonic tissue and used immediately for differentiation. Included are cells listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (Miz-Medi Hospital-Seoul National University); HSF-1, HSF-6 (University of California at San Francisco); and H1, H7, H9, H13, H14 (Wisconsin Alumni Research Foundation (WiCell Research Institute)).

Stem cells of interest also include embryonic cells of various types, exemplified by human embryonic stem (hES) cells, described by Thomson et al. (1998) Science 282:1145; embryonic stem cells from other primates, such as Rhesus stem cells (Thomson et al. (1995) Proc. Natl. Acad. Sci USA 92:7844); marmoset stem cells (Thomson et al. (1996) Biol. Reprod. 55:254); and human embryonic germ (hEG) cells (Shamblott et al., Proc. Natl. Acad. Sci. USA 95:13726, 1998). The stem cells may be obtained from any mammalian species, e.g. human, equine, bovine, porcine, canine, feline, rodent, e.g. mice, rats, hamster, primate, etc.

ES cells are considered to be undifferentiated when they have not committed to a specific differentiation lineage. Such cells display morphological characteristics that distinguish them from differentiated cells of embryo or adult origin. Undifferentiated ES cells are easily recognized by those skilled in the art, and typically appear in the two dimensions of a microscopic view in colonies of cells with high nuclear/cytoplasmic ratios and prominent nucleoli. Undifferentiated ES cells express genes that may be used as markers to detect the presence of undifferentiated cells, and whose polypeptide products may be used as markers for negative selection. For example, see US 2003/0224411 A1; Bhattacharya (2004) Blood 103(8):2956-64; and Thomson (1998), supra., each herein incorporated by reference. Human ES cell lines express cell surface markers that characterize undifferentiated nonhuman primate ES and human EC cells, including stage-specific embryonic antigen (SSEA)-3, SSEA-4, TRA-1-60, TRA-1-81, and alkaline phosphatase. The globo-series glycolipid GL7, which carries the SSEA-4 epitope, is formed by the addition of sialic acid to the globo-series glycolipid Gb5, which carries the SSEA-3 epitope. Thus, GL7 reacts with antibodies to both SSEA-3 and SSEA-4. The undifferentiated human ES cell lines did not stain for SSEA-1, but differentiated cells stained strongly for SSEA-1. Methods for proliferating hES cells in the undifferentiated form are described in WO 99/20741, WO 01/51616, and WO 03/020920.

In the context of cell ontogeny, the adjective "differentiated", or "differentiating" is a relative term. A "differentiated cell" is a cell that has progressed further down the developmental pathway than the cell it is being compared with. Thus, embryonic stem cells can differentiate to lineage-restricted precursor cells, which in turn can differentiate into other types of precursor cells further down the pathway, and then to an end-stage differentiated cell, which plays a characteristic role in a certain tissue type, and may or may not retain the capacity to proliferate further.

The potential of ES cells to give rise to all differentiated cells provides a means of giving rose to any mammalian cell type, and so a very wide range of culture conditions may be used to induce differentiation, and a wide range of markers may be used for selection. One of skill in the art will be able to select markers appropriate for the desired cell type.

Culture medium: The stem or progenitor cells are grown in vitro in an appropriate liquid nutrient medium. Generally, the seeding level will be at least about 10 cells/ml, more usually at least about 100 cells/ml and generally not more than about $10^5$ cells/ml, usually not more than about $10^4$ cells/ml.

Various media are commercially available and may be used, including Ex vivo serum free medium; Dulbecco's Modified Eagle Medium (DMEM), RPMI, Iscove's medium, etc. The medium may be supplemented with serum or with defined additives. Appropriate antibiotics to prevent bacterial growth and other additives, such as pyruvate (0.1-5 mM), glutamine (0.5-5 mM), 2-mercaptoethanol ($1-10\times10^{-5}$ M) may also be included.

Culture in serum-free medium is of particular interest. The medium may be any conventional culture medium, generally supplemented with additives such as iron-saturated transferrin, human serum albumin, soy bean lipids, linoleic acid, cholesterol, alpha thioglycerol, crystalline bovine hemin, etc., that allow for the growth of hematopoietic cells.

Preferably the medium is free of cytokines, bone morphogenetic proteins, and an extracellular matrix component derived from feeder layer cells (for example as described in U.S. Pat. No. 6,800,480), particularly cytokines that induce cellular differentiation. The term cytokine may include lymphokines, monokines and growth factors. Included among the cytokines are thrombopoietin (TPO); nerve growth factors such as NGF-.beta.; platelet-growth factor; transforming growth factors (TGFs) such as TGF-α and TGF-β; erythropoietin (EPO); interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; etc. In some circumstances, proliferative factors that do not induce cellular differentiation may be included in the cultures, e.g. c-kit ligand, LIF, and the like, particularly LIF.

These cells may find various applications for a wide variety of purposes. The cell populations may be used for screening various additives for their effect on growth and the mature differentiation of the cells. In this manner, compounds which are complementary, agonistic, antagonistic or inactive may be screened, determining the effect of the compound in relationship with one or more of the different cytokines.

The populations may be employed as grafts for transplantation. As ES cells are capable of differentiation into all lineages, there are many uses for the cells, including generation of hematopoietic stem and progenitor cells, neural and astrocyte stem and progenitor cells; pancreatic islet cells; cardiac muscle cells and muscle cell progenitors; and the like. For example, hematopoietic cells are used to treat malignancies, bone marrow failure states and congenital metabolic, immunologic and hematologic disorders.

The cells of this invention can be supplied in the form of a pharmaceutical composition, comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition will be adapted in accordance with the route and device used for administration. The composition may also comprise or be accompanied with one or more other ingredients that facilitate the engraftment or functional mobilization of the cells.

The cells are also useful for in vitro assays and screening to detect factors that are active on undifferentiated or differentiating cells. ES cells may also be assayed for factors and agents that alter the apoptotic balance. For example, ES cells may be placed in serum and feeder layer free culture conditions in the presence or absence of a candidate agent, optionally in the presence of LIF, and the ability of the cells to survive and/or expand is determined. Control cultures may include cells comprising a vector for expression of exogenous Bcl-2. Agents that potentiate or mimic anti-apoptotic proteins, or inhibit pro-apoptotic proteins, may allow the unmodified cells to proliferate under these conditions.

Of particular interest are screening assays for agents that are active on human cells. A wide variety of assays may be used for this purpose, including immunoassays for protein binding; determination of cell growth, differentiation and functional activity; production of factors; and the like.

In screening assays for biologically active agents, viruses, etc. the subject cells, usually a culture comprising the subject cells, is contacted with the agent of interest, and the effect of the agent assessed by monitoring output parameters, such as expression of markers, cell viability, and the like. The cells may be freshly isolated, cultured, genetically altered as described above, or the like. The cells may be environmentally induced variants of clonal cultures: e.g. split into independent cultures and grown under distinct conditions, for example with or without virus; in the presence or absence of other cytokines or combinations thereof. The manner in which cells respond to an agent, particularly a pharmacologic agent, including the timing of responses, is an important reflection of the physiologic state of the cell.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

In addition to complex biological agents, such as viruses, candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term samples also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1:1 to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) Trends Biotechnol. 17(12):477-81). Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) Biotechniques 26(1):112-225; Kawamoto et al. (1999) Genome Res 9(12):1305-12; and Chen et al. (1998) Genomics 51 (3):313-24, for examples.

For further elaboration of general techniques useful in the practice of this invention, the practitioner can refer to standard textbooks and reviews in cell biology, tissue culture, embryology, and cardiophysiology. With respect to tissue culture and embryonic stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998).

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Experimental

To prevent ES cells from undergoing apoptosis and simplify the analysis of exogenous factors on self-renewal and differentiation in the absence of serum and feeders, we established ES cell clones constitutively expressing human Bcl-2. The Bcl-2 family of anti-apoptotic proteins has been implicated in the prevention of cell death by sequestering BH3-only pro-apoptotic proteins on the mitochondrial surface, and thus antagonizing multidomain pro-apoptotic proteins. In the analysis of blood cell systems, enforced expression of Bcl-2 helped separate survival effects of certain cytokines from their roles on growth and differentiation, and enabled examination of the effect of single growth factors and cytokines on the self-renewal and differentiation of hematopoietic stem cells in vitro.

Here we show that ES cells constitutively expressing Bcl-2 have a survival advantage in serum- and feeder-free conditions, and that these Bcl-2 clones expand in an undifferentiated state in the absence of serum and feeders when supplemented with LIF.

Materials and Methods

Cell culture. D3 ES cells (Doetschman et al. (1985) J. Embryol. Exp. Morphol. 87:27-45) were maintained as previously described (Yamane et al. (1997) Blood 90:3516-3523), and clones expressing human Bcl-2 were established by co-transfecting parental D3 ES cells with the human Bcl2-IRES-EGFP transgene under control of the CAG promoter, and a puromycin resistance gene cassette. Bcl-2 ES cell clones were selected and expanded in the presence of puromycin. For serum-free cultures, ES cells are maintained in X-VIVO 15 (Cambrex) supplemented with 2 mM GlutaMax-1 (Gibco), 0.1 mM 2-mercaptoethanol, 1,000 U/mL ESGRO (Chemicon International), 100 U/mL penicillin (Gibco), and 100 mg streptomycin (Gibco) on gelatin-coated dishes. Alternatively, IMDM/F12 (1:1) (Gibco) supplemented with 2 mM GlutaMax-1, 0.1 mM 2-mercaptoethanol, 0.1% polyvinyl alcohol (Sigma), 1× Insulin-Transferin-Selenium-X (Gibco), 1,000 U/mL ESGRO, 100 U/mL penicillin, and 100 mg streptomycin was used where indicated. Cells were dissociated with Cell Dissociation Buffer (Enzyme-Free, Hanks'-based, Gibco).

To induce hematopoietic differentiation in vitro, cells were placed on ST2 in MEM alpha media (Gibco) supplemented with 10% FCS. On day 6 of differentiation, colonies are dissociated with 0.25% trypsin/0.5 mM EDTA (Gibco), and replated onto freshly confluent ST2 cells. On day 14 of differentiation, non-adherent cells are harvested by gentle pipeting and replated onto OP9 feeder cells. On day 21, cells are analyzed by flow cytometry. For neuronal induction, cells are placed on AC11 stromal cells and cultured in IMDM supplemented with 2 mM GlutaMax-1, 0.1 mM 2-mercaptoethanol, 0.1 mM dexamethasone (Sigma), 15% FCS, 100 U/mL penicillin, and 100 mg streptomycin and cells are analyzed for neuronal markers following 2 weeks of culture.

Flow cytometry. For intracellular staining, cells were fixed in 1% paraformaldehyde/PBS for 20 min and then permeabilized and blocked using 0.1% saponin/10% FCS for 20 min. Cells were then incubated with primary antibodies against human Bcl-2 (Dako) or Oct-3/4 (BD Bioscience) for one hour, washed, and then stained with phycoerythrin (PE)-conjugated secondary antibodies for 30 min. For hematopoietic analysis, cells were blocked with rat IgG for 20 min, and then incubated with a cocktail of the following PE-conjugated antibodies for 20 min: M1/70 (Mac-1), 8C5 (Gr-1), Ter119. Annexin-V labeling was performed with allophycocyanin (APC)-conjugated annexin-V (Molecular Probes) antibodies according to manufacturer's instruction.

Immunocytochemistry. For immunohistochemical staining, cells were fixed in 4% PFA for 15 min, permeabilized with 0.1% Triton X-100 in PBS for 5 min, and then blocked with 1% BSA in PBS for 15 min. Cells were incubated with primary antibodies against Oct-3/4, class III beta-tubulin (TuJ1, Covance), NeuN (Chemicon International), MAP2 (Chemicon International) overnight, washed, and then incubated with PE or Cy3-conjugated goat anti-mouse IgG secondary antibodies for one hour.

Polymerase Chain Reaction. Quantitative RT-PCR was performed using total RNA isolated from parental murine D3 or Bcl2 ES cells using the RNeasy procedure (Qiagen), after treatment with DNase I for 15 minutes at room temperature, and reverse transcription using poly-dT primers and Superscript™ first strand synthesis system (Invitrogen). Amplification was performed using the Nanog forward 5'-TCTGGGAACGCCTCATCAAT-3' [SEQ ID NO. 1] and reverse 5'-GGAGAGGCAGCCTCTGTGC-3' [SEQ ID NO. 2] Rex-1 forward 5'-GCGACATTTTCTGGTGCACA-3' [SEQ ID NO. 3] and reverse 5'-TCGAACGTGCACTGATACGG-3' [SEQ ID NO. 4], and GAPDH forward 5'-GGCAAATTCAACGGCACAGT-3'[SEQ ID NO. 5] and reverse 5'-TCGCTCCTGGAAGATGGTGAT-3' [SEQ ID NO. 6] primers with 40 cycles of two-step PCR (15 s at 95° C. and 60 s at 60° C.) after initial denaturation (95° C. for 10 mm) using an ABI Prism 7000 Sequence Detector System (Applied Biosystems). Amplification of GAPDH mRNA was used to normalize reactions internally. Each sample was analyzed in duplicate and results are expressed as the mean mRNA expression level±s.e.m relative to parental D3 cells (n=3). For genomic PCR, genomic DNA was isolated by using DNeasy tissue Kit (Qiagen). Amplification was performed using the Sry forward 5'-CAGCCCTACAGCCACATGAT-3' [SEQ ID NO. 7] and reverse 5'-TTTAGCCCTCCGATGAGGC-3' [SEQ ID NO. 8], Actin forward 5'-GTACCACAGGCATTGTGATG-3' [SEQ ID NO. 9] and reverse 5'-TAGTGATGACCTGGCCGTCA-3' [SEQ ID NO. 10] primers with 36 cycles of PCR (45 s at 94° C., 60 s at 56° C., 90 s at 72° C.) after initial denaturation (94° C. for 5 min)

Chimeric mice. Blastocysts were collected from superovulated C57BL/Ka females at E3.5. Injected or non-injected blastocyst were transferred into the uterus of E2.5 pseudo pregnant BCBA/F1 females and all mice were maintained in Stanford University's Research Animal Facility in accordance with Stanford APLAC guidelines.

Western blots. Cells were lysed in 50 mM Tris-Cl (pH7.5)/150 mM NaCl/1% Triton-X/1% protease inhibitor cocktail set III (Calbiochem)/1 mM EDTA/1 mM $Na_3Vo_4$/1 mM NaF and proteins were separated by SDS-PAGE under denaturing conditions and transferred to Immobilon-P membrane (Miilipore). After blocking with 5% milk, the membrane was incubated with primary antibodies against phospho-Smad1/5/8 (Cell Signaling Technology), actin (Sigma), Bcl-2 (Dako), Bcl-xL (BD Bioscience), Mcl-1 (ABGENT), or Bax (BD Bioscience), washed, and then incubated with HRP-conjugated secondary antibodies. Immunoreactive bands were visualized using the ECL™ detection system (Amersham).

MAP kinase inhibitors. 1 μM SB203580 (Calbiochem) and 12.5 μM PD98059 (Calbiochem) were used as described (Qi et al. (2004) Proc. Natl. Acad. Sci USA 101, 6027-6032; Burdon et al. (1999) Dev. Biol. 210, 30-43).

Results

Figure 2:
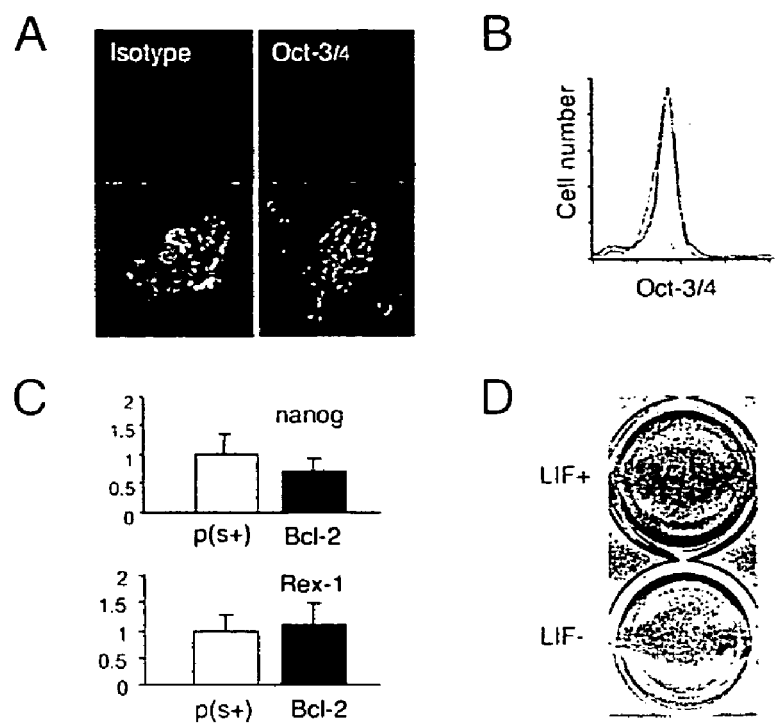
FIG. 2A-2D. Expression of undifferentiated ES cell markers. (A) Cells cultured for 44 days after serum-removal were stained with Oct-3/4 (right panels) or isotype control antibody (left panels). Upper and lower panels show fluorescent and phase contrast images, respectively. (B) Bcl-2 ES cells cultured 45 days without serum and feeders (red) or the parental ES cell line cultured with serum (blue, dashed line) was stained with Oct-3/4 (red, blue) or isotype control antibody (dashed line). (C) The expression levels of nanog and Rex-1 were analyzed in parental D3 cells with serum [p(s+)] and Bcl-2 ES cells cultured for 49 days in serum- and feeder-free conditions (Bcl-2). Gene expression levels are shown following internal normalization with GAPDH and normalization against parental cells (value=1). Values are expressed as means±S.E.M. (D) Alkaline phosphatase activity was assessed in Bcl-2 ES cells grown in serum and feeder-free conditions for 43 days prior to culture with (upper well) or without LIF (lower well) for 6 days in serum-free conditions before staining.

Serum- and feeder-independent growth of ES cells overexpressing Bcl-2. To facilitate examination of cytokine, growth factor, and chemical effects on self-renewal and differentiation of ES cells in the absence of serum and feeders, we established ES cell clones overexpressing human Bcl-2. In these clones, human Bcl-2 expression was driven by the CAG promoter (human cytomegalovirus immediate-early enhancer and a modified chicken beta-actin promoter), followed by enhanced green fluorescent protein (EGFP) encoded after an internal ribosomal entry site (FIG. 1A). This bicistronic construct allows Bcl-2 expressing cells to be traced easily by fluorescence of EGFP (FIG. 2B). In conventional culture conditions containing serum, ES cell clones expressing Bcl-2 and the parental ES cell line grew with similar kinetics.

To confirm that Bcl-2 overexpression provide a survival advantage to the cells, parental and Bcl-2 ES cells were cultured in serum- and feeder-free conditions in X-Vivo media, which contains insulin, transferrin, and albumin as basic supplements for serum-free cultures, but no other proteins or hormone. After three days culture, apoptotic cells were detected by Annexin V. Annexin V binds to phosphatidylserine, a membrane component normally localized to the internal face of the cell membrane, but exposed to the outer surface of the membrane in the apoptotic cells. As shown in FIG. 1C, less Bcl-2 cells were positively labeled with annexin V versus parental ES cells, suggesting that Bcl-2 provides a survival advantage normally supported by factors included in serum or by feeder cells.

Interestingly, Bcl-2 clones continued to proliferate in the presence of LIF alone in X-Vivo media, as demonstrated in FIG. 1D. In contrast, passaging of the parental cell was not possible beyond a couple of passages, despite the presence of LIF. Although Bcl-2-transgenic ES cells grew slowly in the absence of serum and feeder layers compared to culture conditions containing serum, they expanded indefinitely (for at least 2 months). Bcl-2 clones expanded independent of serum and feeders formed tightly packed colonies with indistinct cell boundaries (FIG. 1E); a hallmark of undifferentiated ES cells. Even at low cell density (50 cells/cm2), Bcl-2 cells formed tightly packed undifferentiated colonies in the presence of LIF (FIG. 1F). For the input of 200 cells, 9.5±4.2 undifferentiated colonies were formed after 7 days culture without serum and feeders (FIG. 1G). Parental ES cells never formed colonies at this clonal density (FIG. 1G), suggesting the lack of survival signal from serum and feeders is more critical at low cell density. Not only did Bcl-2 expressing ES cell clones expand in X-Vivo media, but they also grew in IMDM/F-12 media containing insulin and transferrin, but no other proteins or hormones, when supplemented with LIF (FIG. 1H), indicating that growth of Bcl-2 ES cell clones in serum- and feeder-free conditions was not specific to X-Vivo media.

Bcl-2 ES cells are maintained in an undifferentiated state with LIF in the absence of serum and feeders. The tightly packed morphology of Bcl-2 clones in serum- and feeder-free conditions indicated that they were kept in an undifferentiated state. To consolidate this view, the molecular markers for undifferentiated ES cells were examined after extended serum- and feeder-free culture. Oct-3/4, the POU transcription factor required for the formation and maintenance of ES cells, was detected by immunocytochemistry in Bcl-2 ES cell clones cultured in serum and feeder-free conditions (FIG. 2A), and was comparable to parental ES cells cultured in serum as detected by FACS (FIG. 2B). Moreover, gene expression of Nanog, a homeodomain protein required for ES cell pluripotency, and Rex-1, a zinc-finger protein specifically expressed in pluripotent cells, were also similar in the parental ES cell line in conventional conditions and a Bcl-2 clone cultured in the absence of serum and feeders (FIG. 2C). Bcl-2 clones cultured in serum- and feeder-free conditions also contained alkaline phosphatase activity (another marker of pluripotent cells of embryonic origin) in the presence of LIF, but lost this characteristic after the removal of LIF (FIG. 2D). These properties suggest that Bcl-2 expressing ES cell clones expanded in the absence of serum and a feeder layer are maintained in an undifferentiated state, and the requirement for supplemental LIF remains intact.

Pluripotency of Bcl-2 ES cells is maintained in serum- and feeder-free conditions. To determine whether the multilineage potential of ES cells was sustained in Bcl-2 clones growing in the absence of serum and feeders, ES cell differentiation potential was investigated in vitro. Bcl-2 ES cells efficiently generated hematopoietic colonies when sequentially cultured on ST2 and OP9 stromal cell lines (FIG. 3A), and flow-cytometric analysis demonstrated the generation of cells with mature myeloid cell lineage markers (FIG. 3B). In addition, Bcl-2 ES cells efficiently generated neurons, as identified by staining with antibodies against bIII-tubulin, microtubule-associated-protein-2 (MAP2), and neuron specific nuclear protein (NeuN), following culture on AC11 stromal cells in the presence of dexamethasone; a synthetic corticosteroid (Yamane and Weissman, unpublished) (FIG. 3C). These results indicate that Bcl-2 ES cell clones proliferating in serum- and feeder-free conditions maintain their multipotency.

To definitively determine whether Bcl-2 expressing ES cells expanded in the absence of serum and feeders maintain their pluripotency, we checked whether they could contribute to chimeric animals when transplanted into blastocysts. Cells from a Bcl-2 clone cultured in the absence of serum and feeders were injected into blastocysts, and transferred to the uteri of pseudopregnant mice. Mice were sacrificed on E11.5 and checked for the contribution of ES cell-derived cells to the embryo by EGFP expression, wherein fluorescence was detected in the injected blastocyst-derived embryo throughout the body (FIG. 3D). In addition, chimeric mice had Bcl-2 ES cell-derived (i.e. 129 background) agouti coat color (FIG. 3E). Tissue chimerism was investigated in female chimeric mice (as Bcl-2 ES cells have male genotype), wherein the contribution of ES cells can be examined by the presence of Y chromosome genes on the female background. Semi-quantitative PCR analysis for presence of the Sry gene (a Y chromosome gene) using genomic DNA from various tissues demonstrated approximately 30% contribution to all tissues investigated, including the heart, spleen, bone marrow (mesoderm), lung, liver (endoderm), and brain (ectoderm) (FIG. 3F). These results indicate definitively that Bcl-2 ES cells maintained in the absence of serum and feeders are pluripotent.

Figure 4:
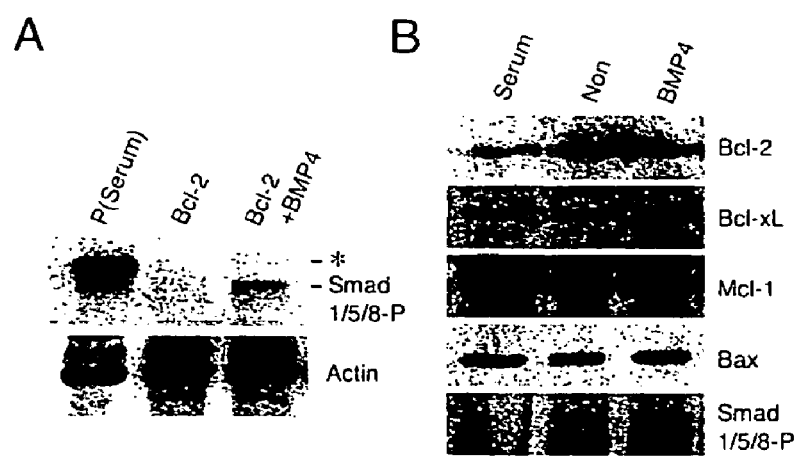
FIG. 4A-4B. Western blot analysis for Smad proteins and Bcl-2 family members. (A) Cell lysates of parental cells cultured in conventional conditions with serum [p(serum)], a Bcl-2 clone in serum and feeder-free conditions untreated (Bcl-2), or treated with BMP4 for 90 minutes (Bcl-2+BMP4) were analyzed for the presence of phospho-Smad1/5/8 by western blotting (upper panel). The same membrane was stripped and reprobed with anti-actin antibody (lower panel). The band denoted by an asterisk is a product of non-specific staining. (B) Western blot analysis of Bcl-2 family members was performed for parental ES cells in conventional conditions with serum (serum), and for parental ES cells in serum- and feeder-free conditions without (Non) or treated with BMP4 for 6 hours (BMP4).

BMP independent self-renewal of Bcl-2 ES cells. Ying et al. recently reported that bone morphogenic proteins (BMPs), or growth and differentiation factors (GDFs), substitute the serum and feeder requirements during the maintenance of ES cells (Ying et al. (2003) Cell 115, 281-292). Nevertheless, our culture media contained only LIF, insulin, transferrin, and albumin as protein components. One possible explanation for the above discrepancy is that Bcl-2 clones secrete these effectors in an autocrine manner. Ying et al. reported that BMP2, BMP4, and GDF-6, but neither TGF-$\beta$1 nor activin, support the self-renewal of ES cells, suggesting that Smad1/5/8 are likely to be downstream targets of these effectors. To test whether BMP/GDF signaling acts in an autocrine fashion in our culture conditions, Western blot analysis was performed for phosphorylated Smad1/5/8. As shown in FIG. 4A, phosphorylated Smad1/5/8 was detected in ES cells cultured in conventional conditions, suggesting serum contained BMP/GDF activity or ES cells secreted these proteins upon serum stimulation. In contrast, the activated form of Smad1/5/8 was not detected in Bcl-2 ES cells in either serum or feeder-free conditions, although they could respond to BMP4 stimulation (FIG. 4A). These results suggest that ES cells overexpressing Bcl-2 self-renew in the presence of LIF independent of BMP activity.

BMP and serum does not regulate Bcl-2 family expression. BMP-independent self-renewal of Bcl-2 clones prompted us to examine whether Bcl-2 family proteins are downstream targets of BMP signaling. We performed Western blot analysis to examine the possibility that expression of anti-apoptotic or pro-apoptotic bcl-2 family members were up- or down-regulated upon BMP/GDF stimulation, respectively, but neither Bcl-2, Bcl-xL, or Mcl-1 anti-apoptotic proteins are up-regulated, nor the Bax pro-apoptotic protein down-regulated by BMP stimulation (FIG. 4B). Importantly, addition of BMP did not improve viability of the parental cell line cultured in serum- and feeder-free conditions. It thus appears unlikely that BMP confers a survival advantage to ES cells, and other factors in serum likely control ES cells survival by a mechanism independent of regulating the expression of Bcl-2 family members, since the removal of serum neither down-regulated Bcl-2, Bcl-xL or Mcl-1 nor up-regulated Bax (FIG. 4B). It is more likely that factors in serum regulate Bcl-2 family members post-translationally (e.g. by phosphorylation) to protect ES cells from apoptosis.

Figure 5:
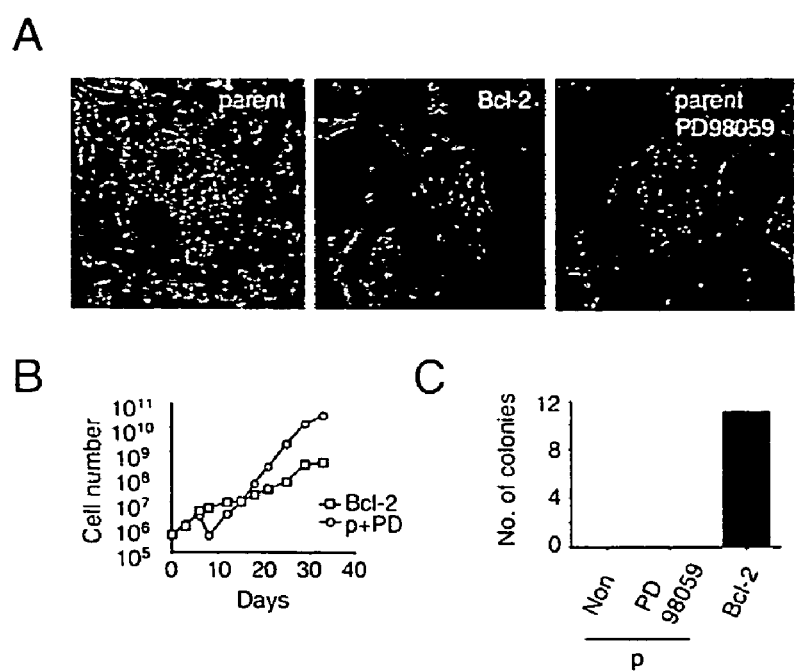
FIG. 5A-5C. Effect of MAPK inhibitors on ES cell self-renewal. (A) Phase contrast image of parental ES cells cultured for 8 days (left), Bcl-2 ES cells cultured for 14 days (middle), and parental ES cells cultured with PD98059 for 14 days (right) in serum- and feeder-free conditions. (B) Growth curve of Bcl-2 ES cells (square) and parental ES cells cultured with 12.5 µM of PD98059 (circle) in serum- and feeder-free conditions. (C) Colony formation activity of parental (p) ES cells cultured without (Non) or with PD98059, and Bcl-2 ES cells at low cell density. Cultures were initiated with 200 cells per well (12 well-plate) and colonies were enumerated 7 days later.

Does Bcl-2 block differentiation? LIF alone has been reported to be insufficient to block differentiation of ES cells, but BMPs in combination with LIF can efficiently block differentiation of ES cells. However, LIF is sufficient to support the self-renewal of Bcl-2 ES cells. A passage prior to unsuccessful propogation of the parental ES cell line, differentiated cells appear at the periphery of each colony (FIG. 5A). This phenomenon supports the possibility that Bcl-2 blocks differentiation; however, Bcl-2 ES cells differentiated in the absence of LIF (FIG. 2D), developed normally in in vitro differentiation assays (FIG. 3A-C), and integrated during embryogenesis (FIG. 3D-F). Silencing of the Bcl-2 transgene in these assays is unlikely, because EGFP expression was always observed during these experiments (FIG. 3D). Thus, if Bcl-2 actively blocks differentiation of ES cells, it must inhibit differentiation very specifically and may be contingent on LIF.

LIF is known to stimulate not only STAT pathway but also MAPK pathways. While the STAT3 pathway mediates self-renewal of ES cells, the ERK MAPK pathway has been demonstrated to promote differentiation of ES cells. LIF also activates p38 MAPK in ES cells, but the effect of this pathway on self-renewal and differentiation of ES cells is not known. Qi et al. recently reported that BMP4 supports self-renewal of embryonic stem cells by inhibiting ERK and p38 MAPK pathways (Qi et al. (2004) Proc. Natl. Acad. Sci USA 101, 6027-6032). To investigate the role of these pathways in Bcl-2 transgenic ES cells, we blocked them using specific inhibitors. Suppression of p38 function by SB 203580 did not show any effect on self-renewal and differentiation of ES cells in serum- and feeder-free conditions, suggesting that p38 MAPK pathway do not affect self-renewal of ES cells. In contrast, blockage of ERK pathway in parental ES cell line by MEK1/2 inhibitor PD98059 dramatically reduced the differentiated cells which appeared during culture (FIG. 5A), and supported the continuous growth in serum- and feeder-free conditions in the presence of LIF even without Bcl-2, although there was a crisis upon continued passaging (FIG. 5B). The growth speed is somewhat faster in parental cell line cultured with PD98059 than Bcl-2 ES cells (FIG. 5B); however, PD98059 could never support the colony formation at low cell density conditions (FIG. 5C). These results support the notion that ERK signaling promotes differentiation of ES cells, and blockage of this pathway allows self-renewal, but ES cells still need Bcl-2 overexpression to survive at low cell density in the absence of extrinsic survival promoting factors. Although it is possible that Bcl-2 or components of serum or provided by feeder layers blocks ERK activity, this is unlikely because the phosphorylation status of ERK was not lower in parental ES cells cultured in conventional condition with serum or in Bcl-2 ES cells cultured in serum- and feeder-free condition compared to parental ES cells cultured without serum and feeders.

By generating ES cell lines overexpressing Bcl-2 that can be cultured in vitro in serum- and feeder-free conditions, we can assess the effect of single growth factors, cytokines, and chemicals on proliferation and differentiation of ES cells. In this study, we demonstrated that LIF is sufficient to support the self-renewal of ES cells in the absence of serum and feeders if cells are protected from apoptosis by Bcl-2 overexpression, thus indicating that survival, proliferation, and blockage of differentiation can be maintained by LIF and Bcl-2 signaling cascades.

Bcl-2 ES cells survive well in the absence of serum and feeders, while parental ES cells become apoptotic and cannot be maintained in vitro (FIG. 1C). ES cells cultured in the presence of serum are protected from apoptosis probably through post-translational phosphorylation modifications, rather than through transcriptional regulation of Bcl-2 family genes, as the gene expression and protein levels of Bcl-2 family members (Bcl-2, Bcl-xL, Mcl-1, and Bax) did not change significantly after the removal of serum (FIG. 4B). Importantly, Mcl-1 deficiency results in peri-implantation embryonic lethality, and Mcl-1-null ES cells cannot be derived in vitro. Thus, Mcl-1 is likely to be the essential endogenous Bcl-2 family member expressed in ES cells, and is supported by our observation by quantitative RT-PCR that Mcl-1 expression is robust in mouse ES cells, whereas Bcl-2 and Bcl-xL expression are minimal. Nevertheless, our results suggest that endogenous Mcl-1 is not sufficient to support survival in serum- and feeder-free conditions.

The phosphatidylinositol 3-kinase (PI3K) pathway has been implicated in ES cell proliferation largely due to studies of ES cells lacking PTEN, a lipid phosphatase that function as negative regulators of PI3K pathway. These cells have enhanced proliferative activity, and furthermore, ES cells lacking ERas, a constitutive active Ras expressed in ES cells which activate PI3K pathway, show significantly reduced proliferative capacity. In serum- and feeder-free conditions, LIF is not presumably important for the proliferation of ES cells because Bcl-2 ES cells still proliferated even in the absence of LIF; although they did differentiate (FIG. 2D). Thus, endogenous Eras activity might promote proliferation of ES cells.

Figure 3:
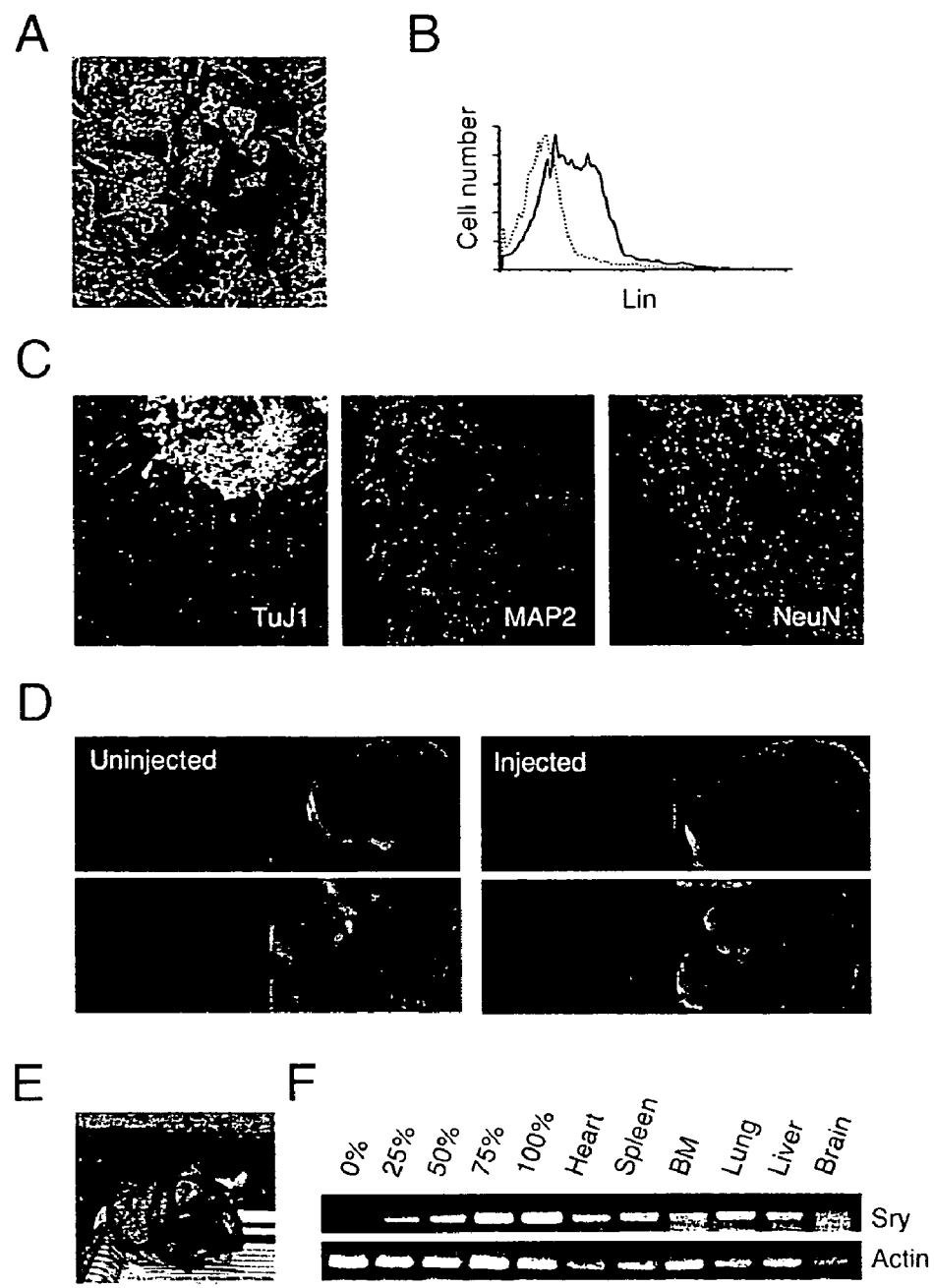
FIG. 3A-3F. Pluripotency of Bcl-2 ES cells growing independently from serum and feeders. (A) Phase contrast image of a hematopoietic cell cluster derived from Bcl-2 ES cells and generated on OP9 feeders following 41 days in serum and feeder-free conditions. (B) Expression of blood cell lineage markers (Lin), including Mac-1, Gr-1, Ter119, as determined by flow cytometry. Dotted line shows isotype control antibody staining levels. (C) Bcl-2 ES cells were induced to differentiate on AC11 following 49 days of serum- and feeder-free culture, and then analyzed for neuronal markers by immunofluorescence. (D) Embryos derived from uninjected blastocysts (left panels) or those injected with Bcl-2 ES cells (right panels) cultured for 45 days without serum and feeders were analyzed for EGFP expression (ES cell-origin) on embryonic day 11.5. Photos of the head (upper panels) and trunk (lower panels) region were taken and each panel shows a fluorescent and bright field image. (E) Picture of a chimeric mouse generated from Bcl-2 ES cells cultured for 31 days without serum and feeders. Agouti coat color denotes Bcl-2 ES cell origin. (F) A female-chimeric mouse was sacrificed to examine Bcl-2 ES cell contributions in various tissues. The Sry gene was used to detect male Bcl-2 ES cell-derived contribution. Standards are 0-100% male genomic DNA diluted in female genomic DNA and actin is shown as a control.

Our results suggest that LIF is sufficient to block the differentiation of ES cells under the condition that ES cells are protected from apoptosis. This is contrast to the report of Ying et al, which shows that LIF is not sufficient to keep ES cells undifferentiated. If Bcl-2 blocks differentiation, it may do so very specifically under serum- and feeder-free conditions, because Bcl-2 ES cells differentiated normally in vitro and in vivo (FIG. 2D, FIG. 3). Interestingly, blocking the ERK pathway using PD98059 reduced differentiation in wild-type ES cell culture and supported continuous growth in serum- and feeder-free conditions in the presence of LIF, although there was a crisis during early passages and PD98059 could not support colony formation at low cell density (FIG. 5A-C). The ERK pathway may be activated by LIF in our serum- and feeder-free conditions. We further examined the possibility that Bcl-2 blocks ERK activation. Western blot analysis showed that Bcl-2 did not inhibit ERK phosphorylation. Importantly, wild-type ES cells cultured with or without serum have similar level of ERK phosphorylation.

We clearly demonstrate here that LIF and Bcl-2 overexpression are sufficient to support the self-renewal of pluripotent stem cells, and the ability to expand ES cells in the absence of serum and feeders will facilitate the investigation of underlying mechanisms for the self-renewal of pluripotent stem cells, and provide a general method for the culture of ES cells.

What is claimed is:

1. A method of expanding mouse undifferentiated embryonic stem cells in the absence of feeder layer cells and the presence of leukemia inhibitory factor (LIF), the method comprising:
   introducing into said stem cells a genetic construct encoding Bcl-2 operably linked to a promoter active in said cells; and
   expanding said mouse undifferentiated embryonic stem cells in a medium free of feeder layer cells and serum, in the presence of LIF, for at least three weeks, while maintaining differentiative capacity.

2. A method of expanding human undifferentiated embryonic stem cells in the absence of feeder layer cells, the method comprising:
   introducing into said stem cells a genetic construct encoding Bcl-2 operably linked to a promoter active in said cells; and
   expanding said human undifferentiated embryonic stem cells in a medium free of feeder layer cells and serum, for at least three weeks, while maintaining differentiative capacity.

3. A method of expanding human or mouse undifferentiated embryonic stem cells in the absence of serum or serum-replacement, the method comprising:
   introducing into said stem cells a genetic construct encoding Bcl-2 operably linked to a promoter active in said cells; and
   expanding said human or mouse undifferentiated embryonic stem cells in a medium free of serum or serum replacement for at least three weeks, while maintaining differentiative capacity.

* * * * *

UNITED STATES PATENT AND TRADEMARK OFFICE
CERTIFICATE OF CORRECTION

PATENT NO.        : 7,641,897 B2
APPLICATION NO. : 11/286088
DATED             : January 5, 2010
INVENTOR(S)       : Weissman et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 398 days.

Signed and Sealed this

Sixteenth Day of November, 2010

David J. Kappos
*Director of the United States Patent and Trademark Office*